United States Patent
Masson et al.

(12) 
(10) Patent No.: US 7,077,805 B1
(45) Date of Patent: Jul. 18, 2006

(54) LIGAMENT RETRACTOR ASSEMBLY FOR USE IN PERFORMING KNEE SURGERY

(75) Inventors: Marcos V. Masson, Houston, TX (US); Mark H. Henry, Houston, TX (US)

(73) Assignee: SI-1, Inc., Conroe, TX (US)

( * ) Notice: Subject to any disclaimer, the term of this patent is extended or adjusted under 35 U.S.C. 154(b) by 0 days.

(21) Appl. No.: 10/109,099

(22) Filed: Mar. 29, 2002

(51) Int. Cl.
*A61B 1/32* (2006.01)

(52) U.S. Cl. .................................... 600/235; 600/210

(58) Field of Classification Search .............. 600/201, 600/210, 211, 213, 214, 226, 227, 229, 235, 600/236, 237, 238, 239, 217, 219; 606/90, 606/105

See application file for complete search history.

(56) References Cited

U.S. PATENT DOCUMENTS

| | | | | |
|---|---|---|---|---|
| 856,352 A | * | 6/1907 | Magoon | 600/210 |
| 2,695,607 A | * | 11/1954 | Hipps et al. | 600/210 |
| 3,731,673 A | * | 5/1973 | Halloran | 600/210 |
| 3,762,401 A | * | 10/1973 | Tupper | 600/210 |
| 3,916,879 A | * | 11/1975 | Cotten | 600/210 |
| 4,520,797 A | | 6/1985 | Petersen | |
| 5,074,865 A | * | 12/1991 | Fahmy | 606/105 |
| 5,307,790 A | * | 5/1994 | Byrne | 600/210 |
| 5,308,350 A | | 5/1994 | Mikhail | |
| 5,334,194 A | | 8/1994 | Mikhail | |
| 5,380,331 A | | 1/1995 | Mikhail | |
| 5,397,330 A | | 3/1995 | Mikhail | |
| 5,964,697 A | | 10/1999 | Fowler | |
| 5,964,698 A | | 10/1999 | Fowler, Jr. | |
| 6,117,072 A | | 9/2000 | Fowler, Jr. | |
| 6,409,731 B1 | * | 6/2002 | Masson et al. | 600/210 |
| 2002/0022211 A1 | * | 2/2002 | Horiguchi | 600/238 |

OTHER PUBLICATIONS

"Retractor Hooks attache to elastic coupler", Surgical Products, Oct. 1999, p. 1.
"Surgical Retractor Hooks", Orthopedic Technology Review, Jan. 2000, and Apr. 2000.
"The Lone Star Retractor System", Journal of Hand Surgery, Jan. 2000.
"The Lone Star Retractor System", Outpatient Surgery Magazine, Jan. 200, Feb. 2000, and Apr. 2000.
"Retract with Ease", Outpatient Surgery Magazine, May 2000.
"The Lone Star Retractor System", Foot & Ankle, Jan. 2000 and Feb. 2000.

* cited by examiner

*Primary Examiner*—Eduardo C. Robert
(74) *Attorney, Agent, or Firm*—Browning Bushman P.C.

(57) ABSTRACT

A ligament retractor assembly including a first retractor paddle, a second retractor paddle and an elastic member having one end received in an opening of the first retractor paddle and an opposite end received by an opening of the second retractor paddle. Each of the first and second retractor paddles includes a retaining section and a lever section. The lever section extends at a generally acute angle with respect to the retaining section. The first and second retractor paddles are integrally formed of a polymeric material. Each of the first and second retractor paddles includes a gripping portion formed at an end of the retaining section adjacent the lever section. The opening is formed on the retaining section of the paddles and has a generally dog leg configuration opening at a side of the retaining section and extending at an angle toward a median of the retaining section. A hole is formed through the retaining section adjacent the opening.

13 Claims, 2 Drawing Sheets

US 7,077,805 B1

LIGAMENT RETRACTOR ASSEMBLY FOR USE IN PERFORMING KNEE SURGERY

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to retractor assemblies as used during surgical procedures. More particularly, the present invention relates to ligament retractors that are used during knee surgery.

BACKGROUND OF THE INVENTION

In performing knee surgery, it is of the utmost importance to avoid or to at least minimize damage to ligaments, tendons, muscles, nerves and other portions of the soft tissue while gaining access to and performing surgical procedures on various portions of the bone structure of the knee. Heretofore, retractors have been utilized in performing knee surgery so as to maximize access to the bone structure intended for osteotomy procedures while, at the same time, providing maximum protection for various soft tissue members. During the knee surgery, an appropriate incision is made along the forward area of the knee joint with the skin and flesh being parted to provide access to the joint. The flesh and the collateral ligaments are typically pulled or retracted laterally to expose the joints and held in this position by a hand held instrument, often referred to as a retractor. These hand-held retractors are held either by the surgeon or his assistant to maintain exposure to the joint to permit surgery to be performed.

In the past, various patents have issued relating to such collateral ligament retractors. For example, U.S. Pat. No. 4,520,797, issued on Jun. 4, 1985 to T. D. Petersen, discloses a collateral ligament retractor for use in knee surgery. This retractor includes a member having a cupped arcuate finger for insertion into the knee joint along and partly around the tibial plateau and a curved portion extending from the finger outwardly along the ligament, then extending back substantially in the same direction as the finger and including a downwardly extending pivoted elongated arm extending to a position behind the knee above the calf. A second member of similar design, but larger to accommodate the everted patella, is positioned around the opposite ligament. A tension member, such as a coil spring, is connected to the outer end of the arms of the members for biasing them toward one another to hold the ligaments in a retracted position.

U.S. Pat. No. 5,334,194, issued on Aug. 2, 1994 to W. W. Mikhail, teaches a collateral ligament retractor for use in performing knee surgery which includes a handle having a flat portion, an integral support section extending from the flat portion of the handle and following a curved path downwardly, and a tip extending from the integral support section and following a curved path in a reverse direction from that of the integral support section. The tip terminates in an end angled upwardly toward and below the plane defined by the horizontally positioned flat portion. The tip has edges tapering toward each other as they approach the end. U.S. Pat. No. 5,397,330, to the same inventor, describes a variation on the ligament retractor of U.S. Pat. No. 5,334,194. U.S. Pat. No. 5,397,330 is particularly utilized in association with posterior cruciate ligament surgery. U.S. Pat. No. 5,380,331, issued on to the same inventor on Jan. 10, 1995, describes a lateral patellar retractor for use in performing knee surgery which has a similar structure in which the support and the prongs are sized to permit the prongs to engage the shelf of the lateral tibial condyle while the support is engaging soft tissue. U.S. Pat. No. 5,308,350, issued to the same inventor on May 3, 1994, shows a femoral distractor for use in knee surgery which includes a rod for insertion in the medullary canal of the femur and a detachable handle assembly. The detachable handle assembly permits the leg of a patient to be moved between positions of extension and flexion without the necessity of removing the rod from the medullary canal.

One of the major problems with these prior art ligament retractors is the fact that they are formed of a rigid steel material and utilize complicated spring-type mechanisms. As such, after each surgery, all of the items involved with the retractor assembly must be sterilized by autoclaving. As a result, the instruments are relatively expensive items. Since they are not disposable, additional costs are associated with the maintenance of such equipment. In other circumstances, since the instruments must be sterilized, they may, on occasion, be unavailable during surgery. Since each of the items described in these prior art patents are relatively expensive items, it is unlikely that the hospital will keep a large supply of such retractors available.

In other circumstances, the spring-type mechanism associated with these retractor assemblies may be inadequate in providing the proper tension to the surfaces being retracted. Since pre-tensioned coil springs are used by the prior art, they may not exert the proper tension required. Furthermore, during the surgical procedures, these prior art retractors do not provide a technique whereby the surgeon can increase the amount of tension applied to the collateral ligament retraction or to decrease the amount of tension. Also, because of the relatively complex nature of these retractor assemblies, the surgeon will require a great deal of time to be completely familiar with the proper operation of such items.

It is an object of the present invention to provide a ligament retractor assembly which is disposable.

It is another object of the present invention to provide a ligament retractor assembly which can assure proper and adjustable tensioning, in an easy manner, during the course of the surgical procedure.

It is another object of the present invention to provide a ligament retractor assembly which does not require sterilization or autoclaving subsequent to surgery.

It is a further object of the present invention to provide a collateral ligament retractor assembly which is easy to use, relatively inexpensive, and easy to manufacture.

These and other objects and advantages of the present invention will become apparent from a reading of the attached specification and appended claims.

BRIEF SUMMARY OF THE INVENTION

The present invention is a ligament retractor assembly comprising a first retractor paddle, a second retractor paddle and an elastic member having one end received by an opening in the first retractor paddle and an opposite end received by an opening in the second retractor paddle. Each of the first and second retractor paddles includes a lever section and a retaining section. The lever section extends at an acute angle from the retaining section. The opening is formed in the retaining section of each of the first and second retractor paddles.

Each of first and second retractor paddles is of an identical configuration. The first and second retractor paddles are each formed integrally of a polymeric material. In the present invention, the elastic member is a length of surgical tubing. The first retractor paddle has a gripping portion formed on an end of the retaining section adjacent the lever section.

The opening associated with each of the first and second retractor paddles includes an entry slot opening at a side of the retractor paddle and extends at an angle toward a median of the retractor paddle, an inward slot communicating with an end of the entry slot opposite the side of the retractor paddle and extending therefrom a distance toward the side of the retractor paddle, and a retaining slot communicating with an end of the inward slot opposite the entry slot. The retaining slot angles toward the median of the retractor paddle. When the surgical tubing is inserted through the entry slot, it can be passed through the inward slot and into the retaining section so as to be fixedly retained within this retaining section. This arrangement prevents accidental release of the surgical tubing during the surgical procedure. A hole is formed in the retaining section adjacent to the opening. The surgical tubing extends through the hole and will be turned backwardly so that the end of the surgical tubing can be inserted into the opening.

In the present invention, the lever section has a concave surface extending therealong. This lever section is generally curved from the retaining section toward an end of the lever section opposite the retaining section. The lever section has scalloping along the concave surface. The scalloping extends transverse to the longitudinal axis of the lever section. The gripping portion has a plurality of ridges extending across the retaining section transverse to the longitudinal axis of the retaining section.

In the present invention, the lever section can be suitably inserted between a ligament and a tibial plateau. The surgical tubing can be suitably inserted into the slot so as to be fixedly retained therein. The other retractor paddle can be placed between the ligament and the opposite side of the tibial plateau. The surgical tubing can be suitably tensioned and then slidably inserted into the slots inserted with the second retractor paddle. As such, the tension associated with the surgical tubing pivots the retractor members about their fulcrum so as to hold the ligaments in a retracted position away from the tibia and to provide access to the knee during surgical procedures.

DETAILED DESCRIPTION OF THE INVENTION

Figure 1:
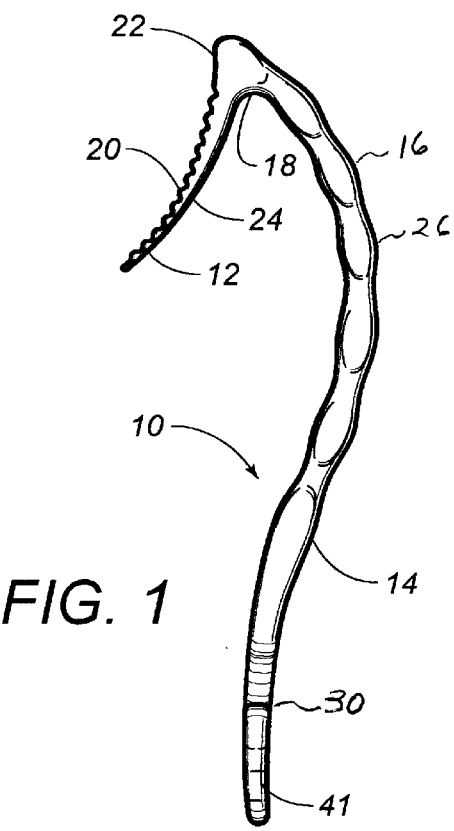
FIG. 1 is a side elevational view showing a ligament retractor paddle in accordance with the teachings of the present invention.

Referring to FIG. 1, there is shown at 10 the ligament retractor paddle in accordance with the teachings of the present invention. The ligament retractor paddle includes a lever section 12 and a retaining section 14. The lever section 12 and the retaining section 14 are integrally formed together of a rigid polymeric material. The lever section extends at an acute angle relative to the retaining section 14. A gripping portion 16 is formed on the surface of the retaining section 14 adjacent to lever section 12.

Since the retractor paddle 10 is formed of a polymeric material, the retractor paddle 10 can be easily disposed of subsequent to surgery. By injection molding the retractor paddle 10 in accordance with proper procedures, a large number of such retractor paddles can be formed at a relatively inexpensive cost. Suitable polymeric materials will provide the proper strength and rigidity to the structure of the retractor paddle 10 so that it is properly functional during knee surgery.

As can be seen in FIG. 1, the lever section 12 has a generally curved configuration extending from the juncture 18 with the retaining section 14. This curved configuration of the lever section 12 will be suitable for fitting against the contour of the curvature of the tibia. As can be seen in FIG. 1, a scalloping 20 will extend along the curved outer surface 22 of the lever section 12. The scalloping 20 will extend transverse to the longitudinal axis of the lever section 12. The scalloping provides a strong grasping surface to the curved surface 22. The opposite side 24 of the lever section 12 can be smooth.

The retaining section 14 extends at any acute angle with respect to the lever section 12. As will be described hereinafter, an opening 30 is formed in the retaining section 14 so that an elastic member can be received therein for retaining the lever section 22 in a properly tensioned relationship against the tibia for the purposes of retracting the ligament associated therewith.

The gripping portion 16 is formed at an end of the retaining section 14 adjacent the lever section 12. The gripping portion 16 is configured for the purposes of manipulation by the surgeon. Several ridges 26 are formed on the inner and outer surfaces of the gripping portion. Ridges 26 define finger indentations therebetween so that a surgeon can have a proper grasp on the gripping portion 16. The structure of the gripping portion 16 enhances the ability to manipulate the retractor paddle 10 during the surgical procedure.

Figure 2:
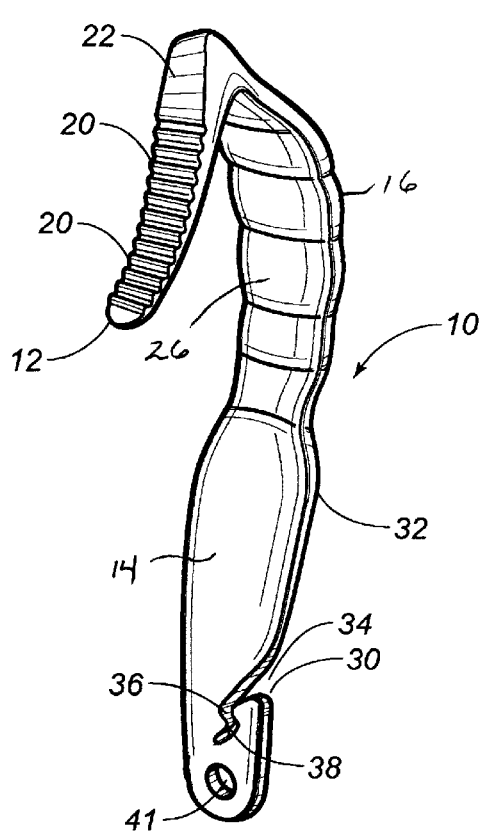
FIG. 2 is a bottom perspective view of the ligament retractor paddle in accordance with the preferred embodiment of the present invention.

FIG. 2 provides a perspective view illustrating the retractor paddle 10. In particular, in FIG. 2, the lever section 12 is particularly illustrated as having concave surface 22. The concave surface 22, along with the scalloping 20, facilitates the ability to properly engage the bone structure. In FIG. 2, the transverse scalloping 20 is particularly illustrated. Similarly, in FIG. 2, the arrangement of the ridges 26 on the handle section 16 are particularly illustrated as extending outwardly from the surface 28.

FIG. 2 shows, with particularity, the opening 30 formed on the retaining section 14. Opening 30 has a generally "dog leg" configuration extending so as to open along edge 32 at a side of the retaining section 14 and to extend inwardly, at an acute angle, toward a median of the retaining section 14.

In particular, the opening 30 includes an entry slot 34 which has one end opening along the edge 32 at the side of the retaining section 14. Entry slot 34 extends inwardly, at an acute angle, toward the median of the retaining section 14. An inward slot 36 communicates with the end of the entry slot 34 opposite the edge 32 and extends back toward the edge 32 for a small distance. A retaining slot 38 has one end communicating with the end of the inward slot 36 opposite the entry slot 34 and returns back toward the median of the retaining section 14. The retaining slot 38 is particularly configured so as to receive the compressed surgical tubing inserted into the opening 30 during the surgical procedure. It is important to note that the "dog leg" structure of the opening 30 assures a secure fixing of the surgical tubing within the slot. This provides a measure of safety so as to prevent accidental release of the surgical tubing from its position within the opening 30 during the surgical procedure. Experiments with the present invention have shown that the circuitous route of the opening 30 will prevent any accidental release of the surgical tubing retained therein.

Hole 41 is formed through the retaining section 14 adjacent to the opening 30. The surgical tubing will be threaded through the hole 41 so as to have an end extending outwardly therefrom. This end can then be inserted through the various slots of opening 30.

Figure 3:
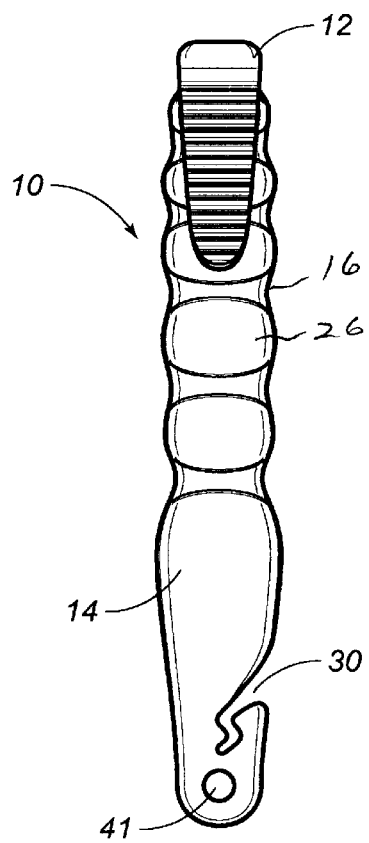
FIG. 3 is an end view of the ligament retractor paddle of the present invention showing, in particular, the opening for the receipt of the surgical tubing therein.

FIG. 3 shows an end view of the retractor paddle 10 as used in the present invention. The gripping portion 16 is located at the end of the retaining section 14 adjacent the lever section 12. The lever section is of tapering width widening toward the retaining section 14. Ridges 26 are illustrated as extending along the inside surface of the retaining section 14.

It is to be noted that during the knee surgery, a pair of retractor paddles 10 are employed during the surgical procedure. A length of surgical tubing is utilized so as to have one end extending through the hole 41 and received within the opening 30 associated with the first retractor paddle and an opposite end extending through a corresponding hole and received within a corresponding opening of the other retractor paddle. By providing proper tension to the surgical tubing, the proper tensioning of the lever sections 12 associated with the retractor paddles is achieved. In the preferred embodiment of the present invention, the other retractor paddle should have an identical configuration to that of a retractor paddle 10. This simplifies and reduces the cost associate with manufacturing. However, it is possible that certain twisting forces caused by the collateral ligaments will require that one of the retractors be a mirror image of the other retractor paddle.

Figure 4:
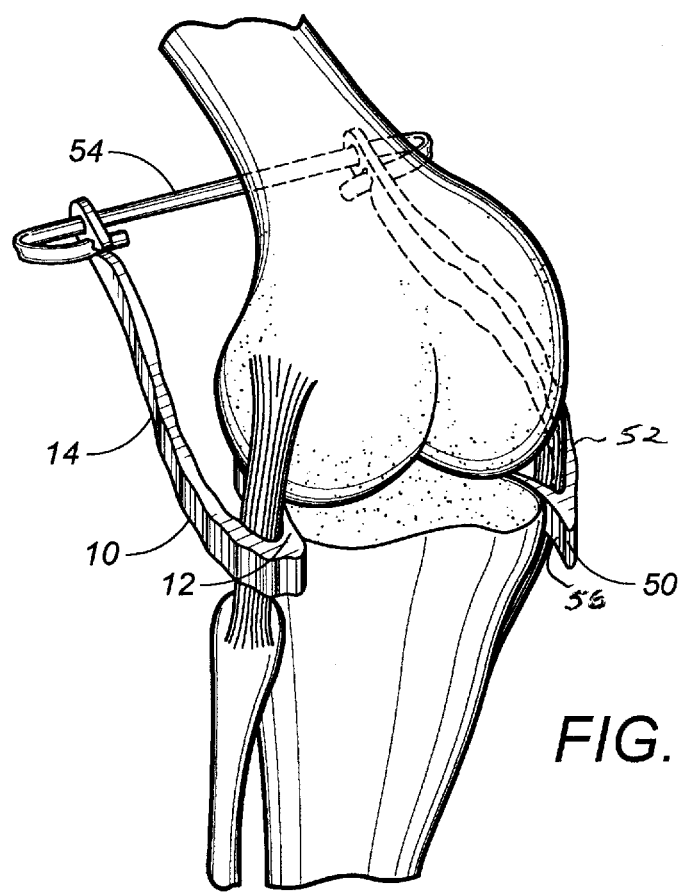
FIG. 4 is a perspective view the use of the ligament retractor assembly of the present invention in association with a knee surgery.

Referring to FIG. 4, there is illustrated a ligament retractor assembly in accordance with the present invention. For the purposes of clarity, only bone structure and the collateral ligaments are illustrated. It should be understood that, during the normal operation, flesh, muscles, and bandages, as well as ligaments, and the everted patella will surround the knee structure with an incision exposing only the front portion of the knee, as seen in FIG. 4.

The retractor assembly of the present invention includes a first retractor paddle 10 and a second retractor paddle 50. The retractor paddle 10 has an identical configuration or a mirror image to that of retractor paddle 50. As can be seen in FIG. 4, retaining section 14 is illustrated as extending outwardly from the lever section 12 of the retractor paddle 10. Similarly, the retaining section 52 extends outwardly from a corresponding lever section 56 on the retractor paddle 50. The retractor members 10 and 50 each have a generally checkmark-shaped configuration, as shown in FIG. 1, including the long curved concave lever section 12 that is adapted to extend along and curve around the tibia to a pivot point. The lever section 12 is concave and curved so as to extend around both in a horizontal and a vertical direction for fitting around the tibial plateau. The retaining section 14 extends outwardly from the lever section 12. The surgical tubing 54 is illustrated as extending through the holes formed in respective retaining sections of the retractor paddles 10 and 50. The end of the surgical tubing is looped backwardly toward the respective retaining sections so that one end of surgical tubing 54 is received within the opening 30 of the retaining section 14. Similarly, the tubing 54 will have an end received by a corresponding opening associated with the retaining section of retractor paddle 50.

Figure 5:
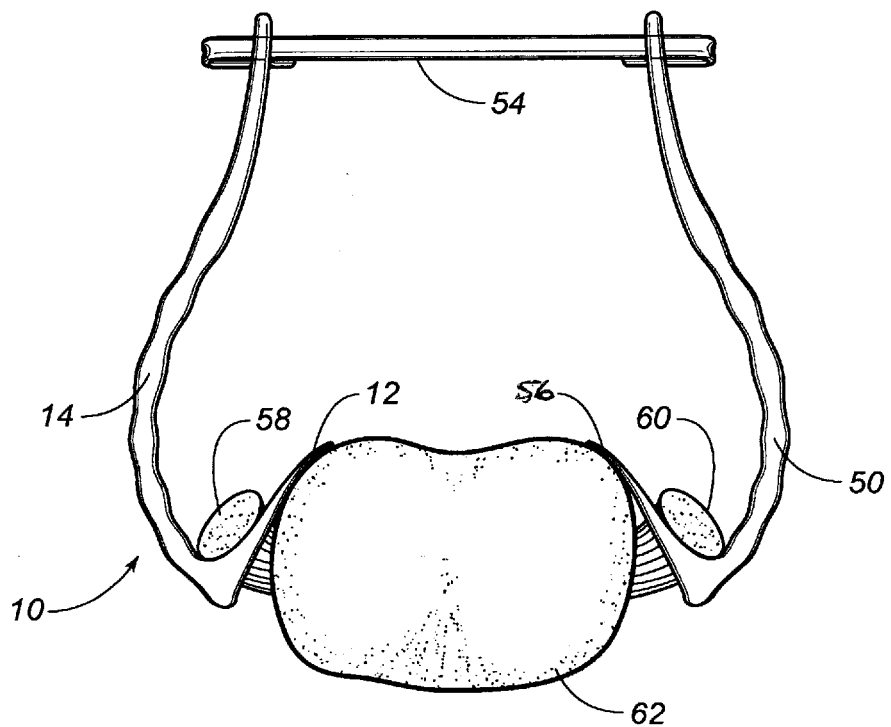
FIG. 5 is a plan view showing the use of the ligament retractor assembly of the present invention in association with a knee surgery.

It will be appreciated that, in viewing FIGS. 4 and 5, that the space between the lever member 12 and the retaining member 14 is filled with the opposed collateral ligaments 58 and 60, flesh, everted patella and bandages or the like (not shown). The above-described material is pulled away from the front of the knee joint and held in a retracted position, as illustrated, by the retractor paddles in the position shown in FIG. 5. The tubing 54 is particularly illustrated in tension so that the collateral ligaments 58 and 60 are separated from the bone structure 62. The combination of the retractor paddles 10 and 50, along with the surgical tubing 54, functions as levers to retract the ligaments. These ligaments are held in position by the tension of the surgical tubing 54 without the aid of the surgeon or assistant. As a result, it frees the hands of the surgeon and his or her assistant for the operation. The pivoted retaining sections 14 and 62 of the respective retractor paddles 10 and 50 enables the lever members 12 and 56 to be positioned so that the knee can be flexed without interfering with the retractor assembly. These pivoting members allow self-adjustment and permanent flexing and extending of the leg or joint as needed. When it is necessary to apply additional retracting force to the collateral ligaments during surgery, the surgical assistant can simply grasp the respective gripping portions and pull. Following that procedure, the surgical assistant can then release the gripping portions. The elastic tubing and the configuration of the retractor paddles assures that the retractor paddles will return to the original position.

The retractor assembly of the present invention provides an effective hands-off retractor that frees the hands of the surgeon for the operation. It can be appreciated that the retractor paddles can be utilized individually and can be hand held. The unique shape and curvature thereof provides a simple and effective retractor that is easily and conveniently utilized for different sizes of knee structure. The retractor assembly of the present invention is somewhat universal and can be used on substantially any size of knee. The retractor assembly of the present invention is of a size having sufficient structural strength and dimensions to perform its function while, at the same time, is small enough to be utilized without interfering with the surgical procedure.

Since the retractor assembly of the present invention utilizes polymeric retractor paddles 10 and 50, along with a length of surgical tubing 54, the retractor paddles 10 and 50 and the surgical tubing 54 can be simply disposed of after use. The present invention avoids the need for autoclaving and sterilization subsequent to surgery. There will always be availability of the retractor assembly of the present invention since large numbers of such retractor assemblies can be easily manufactured and provided at a relatively low cost.

In actual practice, surgeons are often familiar with the tension afforded by surgical tubing. As such, the surgeon will have a better "feel" of the tension applied by the surgical tubing 54 during the surgical procedure. If greater tension is required, the surgeon can simply adjust the tension in the surgical tubing 54 by pulling the surgical tubing from the opening and applying greater tension. If less tension is required, then the surgeon can pull the surgical tubing from the opening and release some of the tension. The amount of tension applied by the surgical tubing 54 is virtually infinitely variable. As such, the surgeon will be given a greater "feel" of the retractor assembly during the surgical procedure.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

We claim:

1. A ligament retractor assembly comprising:
    a first retractor paddle having a lever section and a retaining section, said lever section extending from to said retaining section, and retaining section having an opening therein;
    a second retractor paddle having a lever section and a retaining section, said lever section of said second retractor paddle extending from said retaining section of said second retractor paddle, said retaining section of said second retractor paddle having an opening therein; and
    an elastic member having one end received by said opening of said first retractor paddle and an opposite end received by said opening of said second retractor paddle.

2. The assembly of claim 1, each of said first and second retractor paddles being of an identical configuration.

3. The assembly of claim 1, each of said first and second retractor paddles being a mirror image of each other.

4. The assembly of claim 1, each of said first and second retractor paddles being formed of a polymeric material.

5. The assembly of claim 1, said elastic member being a length of surgical tubing.

6. The assembly of claim 1, said first retractor paddle having a gripping portion formed at an end of said retaining section adjacent said lever section.

7. The assembly of claim 6, said gripping portion having a plurality of ridges extending across said retaining section transverse to a longitudinal axis of said handle section.

8. The assembly of claim 1, said lever section and said retaining section of said first retractor paddle being integrally formed together of a polymeric material.

9. The assembly of claim 1, said opening of said first retractor paddle comprising:
    an entry slot opening at a side of said first retractor paddle and extending at an angle toward a median of said first retractor paddle;
    an inward slot communicating with an end of said entry slot opposite said side of said first retractor paddle and extending therefrom at a distance toward said side of said first retractor paddle; and
    a retaining slot communicating with an end of said inward slot opposite said entry slot, said retaining slot angling toward said median of said first retractor paddle.

10. The assembly of claim 1, said lever section having a concave surface extending therealong, said lever section being generally curved from said retaining section to an end of said lever section opposite said retaining section.

11. The assembly of claim 10, said lever section having scalloping extending across said concave surface, said scalloping extending transverse to a longitudinal axis of said lever section.

12. The assembly of claim 1, said first retractor paddle having a hole formed through said retaining section of said first retractor paddle adjacent said opening of said first retractor paddle, said second retractor paddle having a hole formed through said retaining section of said second retractor paddle adjacent said opening of said second retractor paddle, said elastic member extending through said hole of said first retractor paddle and through said hole of said second retractor paddle.

13. The assembly of claim 1, each of said first and second retractor paddles having a generally checkmark-shaped configuration.

* * * * *